(12) United States Patent
Schelberger et al.

(10) Patent No.: US 6,303,599 B1
(45) Date of Patent: Oct. 16, 2001

(54) FUNGICIDAL MIXTURES

(75) Inventors: Klaus Schelberger, Gönnheim; Reinhold Saur, Böhl-Iggelheim; Hubert Sauter, Mannheim; Bernd Müller, Frankenthal; Erich Birner, Altleiningen; Joachim Leyendecker, Hassloch; Manfred Hampel, Neustadt; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/424,918

(22) PCT Filed: Jun. 2, 1998

(86) PCT No.: PCT/EP98/03282

§ 371 Date: Dec. 1, 1999

§ 102(e) Date: Dec. 1, 1999

(87) PCT Pub. No.: WO98/54970

PCT Pub. Date: Dec. 10, 1998

(30) Foreign Application Priority Data

Jun. 4, 1997 (DE) .............................................. 197 23 289

(51) Int. Cl.[7] ........................ A61K 31/535; A01N 43/40; A01N 43/54; A01N 43/56; A01N 43/64

(52) U.S. Cl. .................................... 514/231.2; 514/239.5; 514/317; 514/384; 514/269; 514/407; 514/522; 514/539; 514/543; 514/619

(58) Field of Search ..................................... 514/407, 384, 514/619, 239.5, 231.2, 317, 539, 522, 543, 269

(56) References Cited

U.S. PATENT DOCUMENTS

| | | | |
|---|---|---|---|
| 4,829,085 | 5/1989 | Wenderoth et al. | 514/522 |
| 5,242,920 | 9/1993 | Sauter et al. | 514/239 |

(List continued on next page.)

FOREIGN PATENT DOCUMENTS

| | | |
|---|---|---|
| 296 38 651 | 2/1997 | (DE) . |
| 0 253 213 | 1/1988 | (EP) . |

(List continued on next page.)

*Primary Examiner*—Allen J. Robinson
(74) *Attorney, Agent, or Firm*—Keil & Weinkauf

(57) ABSTRACT

A fungicidal mixture comprises a.1) a carbamate of the formula I.a,

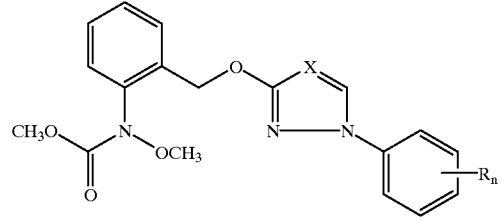

I.a in which X is CH or N, n is 0, 1 or 2 and R is halogen, $C_1$–$C_4$-alkyl or $C_1$–$C_4$-haloalkyl, it being possible for the radicals R to be different if n is 2, or a.2) the oxime ether carboxamide of the formula I.b

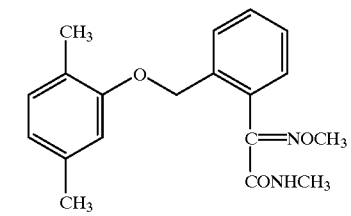

I.b and b.1) 4-[2-methyl-3-(4-tert-butylphenyl)propyl]-2,6-dimethylmorpholine

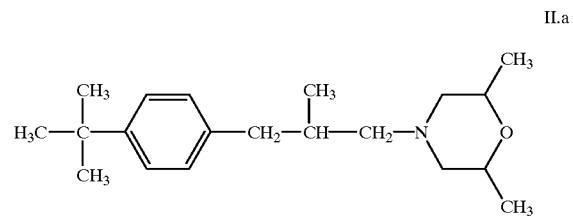

II.a or b.2) 4-($C_{10}$–$C_{13}$-alkyl)-2,6-dimethylmorpholine

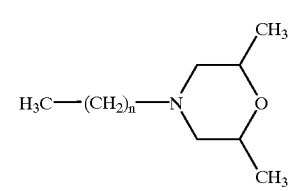

II.b

[$n$ = 10, 11, 12(60–70%), 13]

or b.3) (RS)-1-[3-(4-tert-butylphenyl)-2-methylpropyl]piperidine

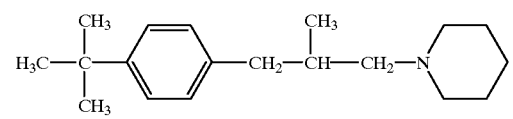

II.c and c) a further active ingredient from the class of the strobilurin fungicides (III), in a synergistically effective amount.

10 Claims, No Drawings

U.S. PATENT DOCUMENTS

| | | | |
|---|---|---|---|
| 5,395,854 | 3/1995 | Brand et al. | 514/619 |
| 5,554,616 | 9/1996 | Wingert et al. | 514/269 |
| 6,136,802 | 10/2000 | Mueller et al. | 514/231 |
| 6,180,638 | 1/2001 | Mueller et al. | 514/269 |

FOREIGN PATENT DOCUMENTS

| | | |
|---|---|---|
| 0 254 426 | 1/1988 | (EP). |
| 0 382 375 | 8/1990 | (EP). |
| 0 477 631 | 4/1992 | (EP). |
| 477631 | 4/1992 | (EP). |
| 0 737 421 | 10/1996 | (EP). |
| 2 742 633 | 6/1997 | (FR). |
| 95/18789 | 7/1995 | (WO). |
| 95/21153 | 8/1995 | (WO). |
| 95/21154 | 8/1995 | (WO). |
| 96/01256 | 1/1996 | (WO). |
| 96/01258 | 1/1996 | (WO). |
| 97/40673 | 1/1997 | (WO). |
| 97/06679 | 2/1997 | (WO). |
| 97/06681 | 2/1997 | (WO). |

FUNGICIDAL MIXTURES

This application is a 371 of PCT/EP98/032 86, filed Jun. 02, 1998.

The present invention relates to a fungicidal mixture which comprises a.1) a carbamate of the formula I.a,

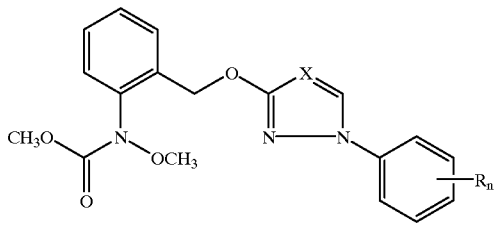

in which X is CH or N, n is 0, 1 or 2 and R is halogen, $C_1$–$C_4$-alkyl or $C_1$–$C_4$-haloalkyl, it being possible for the radicals R to be different if n is 2, or a.2) the oxime ether carboxamide of the formula I.b

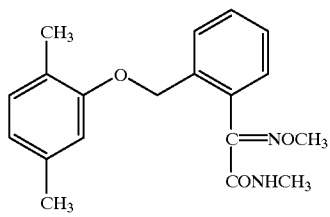

and b.1) 4-[2-methyl-3-(4-tert-butylphenyl)propyl]-2,6-dimethylmorpholine

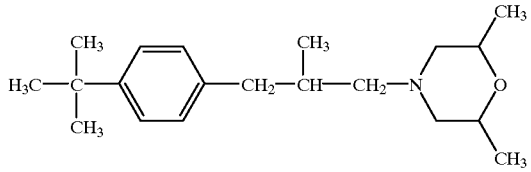

or b.2) 4-($C_{10}$–$C_{13}$-alkyl)-2,6-dimethylmorpholine

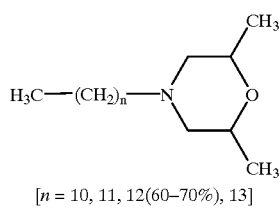

[n = 10, 11, 12(60–70%), 13]

or b.3) (RS)-1-[3-(4-tert-butylphenyl)-2-methylpropyl]-piperidine

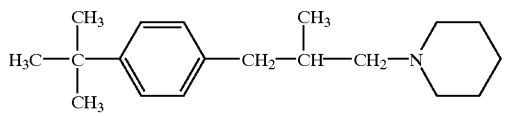

and c) a further active ingredient from the class of the strobilurin fungicides (III), in a synergistically effective amount.

Particular preference is given to mixtures which comprise, as strobilurin fungicide (III), a III.1 methyl phenylacetate of the formula III.1

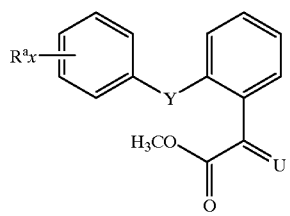

in which U is $CHOCH_3$ or $NOCH_3$, $R^a$ is cyano, halogen, $C_1$–$C_4$-alkyl or $C_1$–$C_4$-haloalkyl, x is 1, 2 or 3, it being possible for the radicals $R^a$ to be different if x is 2 or 3, and Y is one of the radicals $OCH_2$ or O-(4,6-pyrimidinyl)-O, or a III.1 benzyloxybisoxime of the formula III.2

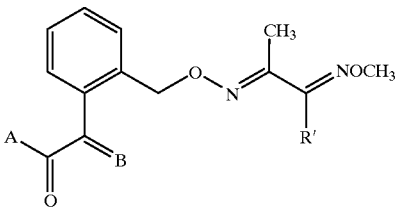

where:

A is $OCH_3$ or $NHCH_3$;
B is $CHOCH_3$ or $NOCH_3$;
R' is phenyl which may carry one to three of the following substituents: cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio; or $C_1$–$C_6$-alkoxy, $C_1$–$C_6$-alkylthio, $C_1$–$C_6$-alkylamino, di-$C_1$–$C_6$-alkylamino, $C_1$–$C_6$-haloalkyloxy, $C_1$–$C_6$-haloalkylthio, $C_1$–$C_6$-haloalkylamino, N—$C_1$–$C_6$-haloalkyl-N—$C_1$–$C_4$-alkylamino, $C_3$–$C_6$-alkenyloxy, $C_3$–$C_6$-alkenylthio, $C_3$–$C_6$-alkenylamino, N—$C_3$–$C_6$-alkenyl-N—$C_1$–$C_4$-alkylamino, $C_2$–$C_6$-haloalkenyloxy, $C_2$–$C_6$-haloalkenylthio, $C_2$–$C_6$-haloalkenylamino, N—$C_2$–$C_6$-haloalkenyl-N—$C_1$–$C_4$-alkylamino, $C_3$–$C_6$-alkynyloxy, $C_3$–$C_6$-alkynylthio, $C_3$–$C_6$-alkynylamino, N—$C_3$–$C_6$-alkynyl-N—$C_1$–$C_4$-alkylamino, $C_3$–$C_6$-haloalkynyloxy, $C_3$–$C_6$-haloalkynylthio, $C_3$–$C_6$-haloalkynylamino, N—$C_3$–$C_6$-haloalkynyl-N—$C_1$–$C_4$-alkylamino, $C_3$–$C_6$-cycloalkyl-methoxy, $C_3$–$C_6$-cycloalkyl-methylthio, $C_3$–$C_6$-cycloalkyl-methylamino, N—$C_3$-$C_6$-cycloalkyl-methyl-N—$C_1$-$C_4$-alkylamino, or benzyloxy, benzylthio, benzylamino, N-benzyl-N—$C_1$-$C_4$-alkylamino, it being possible for the phenyl groups to be partially or fully halogenated and/or to carry one to three of the following radicals: cyano, $C_1$-$C_4$-alkyl, $C_1$-$C_4$-haloalkyl, $C_1$-$C_4$-alkoxy, $C_1$-$C_4$-haloalkoxy and $C_1$-$C_4$-alkylthio.

Moreover, the invention relates to methods for controlling harmful fungi using mixtures of the compounds I (I.a and I.b), II (II.a to II.c) and III (III.1 and III.2).

The compounds of the formula I, their preparation and their activity against harmful fungi are disclosed in the literature (EP-A 477 631; WO-A 96/01,256; WO-A 96/01, 258).

The compounds of the formula II are also disclosed:

II.a (common name: fenpropimorph): CAS RN [67564-91-4], U.S. Pat. No. 4,202,894;

II.b (common name: tridemorph): CAS RN [81412-43-3], DE-A 11 64 152;

II.c (common name: fenpropidin): CAS RN [67306-00-7], U.S. Pat. No. 4,202,894.

Furthermore, the strobilurin fungicides III are disclosed in the literature as active compounds for controlling harmful fungi:

oxime ether ester III.1: EP-A 253 213, EP-A 254 426 and EP-A 382 375;

benzyloxybisoximes of the formula III.2: WO-A 95/18, 789, WO-A 95/21,153, WO-A 95/21,154 and DE P 195 28 651.0.

Synergistic mixtures of the compounds I.a with active compounds II.a to II.c are disclosed in the earlier application DE-A 19 616 724.

Furthermore, EP-A 645 087 discloses synergistic mixtures of the compound I.b with active compounds II.a to II.c.

It is an object of the present invention to provide mixtures which have an improved activity against harmful fungi combined with a reduced total amount of active ingredient applied (synergistic mixtures), with a view to reducing the application rates and to improving the activity spectrum of the known compounds I, II and III.

We have found that this object is achieved by the mixture defined at the outset. Moreover, we have found that better control of harmful fungi is possible by applying the compounds I, II and III simultaneously, that is either together or separately, or by applying the compounds I, II and III in succession than when the individual compounds are used.

The formula I.a in particular represents carbamates in which the combination of the substituents corresponds to a row of Table 1 below:

TABLE 1

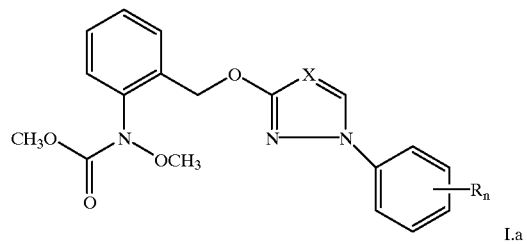

I.a

| No. | X | $R_n$ |
|---|---|---|
| Ia.1 | N | 2-F |
| Ia.2 | N | 3-F |

TABLE 1-continued

| No. | X | $R_n$ |
|---|---|---|
| Ia.3 | N | 4-F |
| Ia.4 | N | 2-Cl |
| Ia.5 | N | 3-Cl |
| Ia.6 | N | 4-Cl |
| Ia.7 | N | 2-Br |
| Ia.8 | N | 3-Br |
| Ia.9 | N | 4-Br |
| Ia.10 | N | 2-$CH_3$ |
| Ia.11 | N | 3-$CH_3$ |
| Ia.12 | N | 4-$CH_3$ |
| Ia.13 | N | 2-$CH_2CH_3$ |
| Ia.14 | N | 3-$CH_2CH_3$ |
| Ia.15 | N | 4-$CH_2CH_3$ |
| Ia.16 | N | 2-$CH(CH_3)_2$ |
| Ia.17 | N | 3-$CH(CH_3)_2$ |
| Ia.18 | N | 4-$CH(CH_3)_2$ |
| Ia.19 | N | 2-$CF_3$ |
| Ia.20 | N | 3-$CF_3$ |
| Ia.21 | N | 4-$CF_3$ |
| Ia.22 | N | 2,4-$F_2$ |
| Ia.23 | N | 2,4-$Cl_2$ |
| Ia.24 | N | 3,4-$Cl_2$ |
| Ia.25 | N | 2-Cl, 4-$CH_3$ |
| Ia.26 | N | 3-Cl, 4-$CH_3$ |
| Ia.27 | CH | 2-F |
| Ia.28 | CH | 3-F |
| Ia.29 | CH | 4-F |
| Ia.30 | CH | 2-Cl |
| Ia.31 | CH | 3-Cl |
| Ia.32 | CH | 4-Cl |
| Ia.33 | CH | 2-Br |
| Ia.34 | CH | 3-Br |
| Ia.35 | CH | 4-Br |
| Ia.36 | CH | 2-$CH_3$ |
| Ia.37 | CH | 3-$CH_3$ |
| Ia.38 | CH | 4-$CH_3$ |
| Ia.39 | CH | 2-$CH_2CH_3$ |
| Ia.40 | CH | 3-$CH_2CH_3$ |
| Ia.41 | CH | 4-$CH_2CH_3$ |
| Ia.42 | CH | 2-$CH(CH_3)_2$ |
| Ia.43 | CH | 3-$CH(CH_3)_2$ |
| Ia.44 | CH | 4-$CH(CH_3)_2$ |
| Ia.45 | CH | 2-$CF_3$ |
| Ia.46 | CH | 3-$CF_3$ |
| Ia.47 | CH | 4-$CF_3$ |
| Ia.48 | CH | 2,4-$F_2$ |
| Ia.49 | CH | 2,4-$Cl_2$ |
| Ia.50 | CH | 3,4-$Cl_2$ |
| Ia.51 | CH | 2-Cl, 4-$CH_3$ |
| Ia.52 | CH | 3-Cl, 4-$CH_3$ |

Particular preference is given to the compounds Ia.12, Ia.23, Ia.32 and Ia.38.

The formula III.1 in particular represents methyl phenylacetates in which the combination of the substituents corresponds to a row of Table 2 below:

TABLE 2

R$^a$X—[phenyl]—Y—[phenyl]—C(=U)—C(=O)—OCH$_3$  III.1

| No. | U | Y | R$^a_x$ |
|---|---|---|---|
| III-1.1 | NOCH$_3$ | OCH$_2$ | 2-CH$_3$ |
| III-1.2 | NOCH$_3$ | OCH$_2$ | 2,5-(CH$_3$)$_2$ |
| III-1.3 | NOCH$_3$ | OCH$_2$ | 2-Cl |
| III-1.4 | NOCH$_3$ | OCH$_2$ | 2-Cl, 5-CH$_3$ |
| III-1.5 | NOCH$_3$ | OCH$_2$ | 5-Cl, 2-CH$_3$ |
| III-1.6 | CHOCH$_3$ | O-[4,6-pyrimidinediyl]-O | 2-CN |
| III-1.7 | CHOCH$_3$ | O-(4,6-pyrimidinediyl]-O | 3-CN |
| III-1.8 | CHOCH$_3$ | O-(4,6-pyrimidinediyl]-O | 4-CN |

Particular preference is given to the compounds III-1.1 and III-1.6.

The formula III.2 in particular represents benzyloxybisoximes in which the combination of the substituents corresponds to one row of Table 3 below:

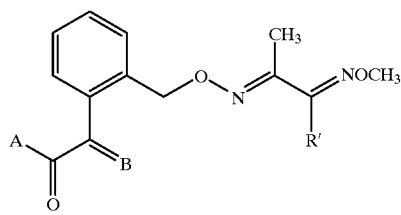

III.2

| No. | A | B | R' |
|---|---|---|---|
| III-2.1 | NHCH$_3$ | NOCH$_3$ | C$_6$H$_5$ |
| III-2.2 | NHCH$_3$ | NOCH$_3$ | 4-F—C$_6$H$_4$ |
| III-2.3 | NHCH$_3$ | NOCH$_3$ | 4-Cl—C$_6$H$_4$ |
| III-2.4 | NHCH$_3$ | NOCH$_3$ | 4-Br—C$_6$H$_4$ |
| III-2.5 | NHCH$_3$ | NOCH$_3$ | 4-I—C$_6$H$_4$ |
| III-2.6 | NHCH$_3$ | NOCH$_3$ | O-CH$_2$CH$_2$CH$_3$ |
| III-2.7 | NHCH$_3$ | NOCH$_3$ | O-CH(CH$_3$)$_2$ |
| III-2.8 | NHCH$_3$ | NOCH$_3$ | O-CH$_2$CH$_2$CH$_2$CH$_3$ |
| III-2.9 | NHCH$_3$ | NOCH$_3$ | O-CH(CH$_3$)CH$_2$CH$_3$ |
| III-2.10 | NHCH$_3$ | NOCH$_3$ | O-CH$_2$CH(CH$_3$)$_2$ |
| III-2.11 | NHCH$_3$ | NOCH$_3$ | O—C(CH$_3$)$_3$ |
| III-2.12 | NHCH$_3$ | NOCH$_3$ | S—C(CH$_3$)$_3$ |
| III-2.13 | NHCH$_3$ | NOCH$_3$ | O-CH(CH$_3$)CH$_2$CH$_2$CH$_3$ |
| III-2.14 | NHCH$_3$ | NOCH$_3$ | O-CH$_2$C(CH$_3$)$_3$ |
| III-2.15 | NHCH$_3$ | NOCH$_3$ | O-CH$_2$C(Cl)=CCl$_2$ |
| III-2.16 | NHCH$_3$ | NOCH$_3$ | O-CH$_2$CH=CH-Cl (trans) |
| III-2.17 | NHCH$_3$ | NOCH$_3$ | O-CH$_2$-C(CH$_3$)=CH$_2$ |
| III-2.18 | NHCH$_3$ | NOCH$_3$ | O-CH$_2$-(cyclopropyl) |
| III-2.19 | NHCH$_3$ | NOCH$_3$ | O-CH$_2$-C$_6$H$_5$ |
| III-2.20 | NHCH$_3$ | NOCH$_3$ | O-CH$_2$-[4-F—C$_6$H$_4$] |
| III-2.21 | NHCH$_3$ | NOCH$_3$ | O-CH$_2$CH$_3$ |
| III-2.22 | NHCH$_3$ | NOCH$_3$ | O-CH(CH$_2$CH$_3$)$_2$ |
| III-2.23 | OCH$_3$ | CHOCH$_3$ | O-CH$_2$CH$_2$CH$_3$ |
| III-2.24 | OCH$_3$ | CHOCH$_3$ | O-CH(CH$_3$)$_2$ |
| III-2.25 | OCH$_3$ | CHOCH$_3$ | O-CH$_2$CH$_2$CH$_2$CH$_3$ |
| III-2.26 | OCH$_3$ | CHOCH$_3$ | O-CH(CH$_3$)CH$_2$CH$_3$ |
| III-2.27 | OCH$_3$ | CHOCH$_3$ | O-CH$_2$CH(CH$_3$)$_2$ |
| III-2.28 | OCH$_3$ | CHOCH$_3$ | O—C(CH$_3$)$_3$ |
| III-2.29 | OCH$_3$ | CHOCH$_3$ | S—C(CH$_3$)$_3$ |
| III-2.30 | OCH$_3$ | CHOCH$_3$ | O-CH(CH$_3$)CH$_2$CH$_2$CH$_3$ |
| III-2.31 | OCH$_3$ | CHOCH$_3$ | O-CH$_2$C(CH$_3$)$_3$ |
| III-2.32 | OCH$_3$ | CHOCH$_3$ | O-CH$_2$C(Cl)=CCl$_2$ |
| III-2.33 | OCH$_3$ | CHOCH$_3$ | O-CH$_2$CH=CH-Cl (trans) |
| III-2.34 | OCH$_3$ | CHOCH$_3$ | O-CH$_2$-C(CH$_3$)=CH$_2$ |
| III-2.35 | OCH$_3$ | CHOCH$_3$ | O-CH$_2$-(cyclopropyl) |
| III-2.36 | OCH$_3$ | CHOCH$_3$ | O-CH$_2$-C$_6$H$_5$ |
| III-2.37 | OCH$_3$ | CHOCH$_3$ | O-CH$_2$-[4-F—C$_6$H$_4$] |
| III-2.38 | OCH$_3$ | CHOCH$_3$ | O-CH$_2$CH$_3$ |
| III-2.39 | OCH$_3$ | CHOCH$_3$ | O-CH(CH$_2$CH$_3$)$_2$ |

Particular preference is given to compounds III-2.1, III-2.2, III-2.3 and to those compounds III-2 in which R' is C$_1$–C$_6$-alkoxy or is benzyloxy with or without substitution by halogen.

Owing to the basic character of their nitrogen atoms, the compounds I, II and III are capable of forming salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals such as phenyl and naphthyl, which carry one or two sulfo groups), alkylphosphonic acids (phosphonic acids having straight-chain or branched alkyl radicals of 1 to 20 carbon atoms), arylphosphonic acids or aryldiphosphonic acids (aromatic radicals such as phenyl and naphthyl, which carry one or two phosphonic acid radicals), it being possible for the alkyl or aryl radicals to carry further substituents, eg. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the first to eighth sub-groups, in particular chromium, manganese, iron, cobalt, nickel, copper, zinc, and furthermore of the second main group, in particular calcium and magnesium, and of the third and fourth main groups, in particular aluminum, tin and lead. The metals can exist in the various valencies which they can assume.

When preparing the mixtures, it is preferred to employ the pure active ingredients I, II and III, to which further active ingredients against harmful fungi or other pests, such as insects, arachnids or nematodes, or else herbicidal or growth-regulating active ingredients or fertilizers can be admixed.

The mixtures of the compounds I, II and III, or the compounds I, II and III applied simultaneously, either together or separately, exhibit outstanding activity against a wide range of phytopathogenic fungi, in particular from the classes of the Ascomycetes, Basidiomycetes, Phycomycetes and Deuteromycetes. Some of them act systemically and can therefore be employed as foliar- and soil-acting fungicides.

They are especially important for controlling a large number of fungi in a variety of crop plants, such as cotton, vegetable species (e.g. cucumbers, beans, tomatoes, potatoes and cucurbits), barley, grass, oats, bananas, coffee, maize, fruit species, rice, rye, soya, grapevine, wheat, ornmentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, Pseudoperonospora species in hops and cucumbers, Alternaria species in vegetables and fruit, Mycosphaerella species in bananas and Fusarium and Verticillium species.

Furthermore they can be used in the protection of materials (eg. in the protection of wood), for example against *Paecilomyces variotii*.

The compounds I, II and III can be applied simultaneously, that is either together or separately, or in succession, the sequence, in the case of separate application, generally not having any effect on the result of the control measures.

The compounds I and II are usually used in a weight ratio of 10:1 to 0.01:1, preferably 5:1 to 0.05:1, in particular 1:1 to 0.05:1.

The compounds I and III are usually used in a weight ratio of 10:1 to 0.01:1, preferably 5:1 to 0.05:1, in particular 1:1 to 0.05:1.

Depending on the kind of effect desired, the application rates of the mixtures according to the invention are, in particular in agricultural crops, from 0.01 to 8 kg/ha, preferably 0.1 to 5 kg/ha, in particular 0.2 to 3.0 kg/ha.

The application rates of the compounds I are from 0.01 to 2.5 kg/ha, preferably 0.05 to 2.5 kg/ha, in particular 0.1 to 1.0 kg/ha.

Correspondingly, in the case of the compounds II, the application rates are from 0.01 to 10 kg/ha, preferably 0.05 to 5 kg/ha, in particular 0.05 to 2.0 kg/ha.

Correspondingly, in the case of the compounds III, the application rates are from 0 01 to 10 kg/ha, preferably 0.05 to 5 kg/ha, in particular 0.05 to 2.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I, II and III, or of the mixtures of the compounds I, II, and III is effected by spraying of dusting the seeds, the plants or the soils before or after sowing of the plants, or before or after plant emergence.

The fungicidal synergistic mixtures according to the invention, or the compounds I, II, and III, can be formulated for example in the form of ready-to-spray solutions, powers and suspensions or in the form of highly concentrated aqueous, oily or other suspensions, dispersions, emulsions, oil dispersions, pastes, dusts, materials for broadcasting or granules, and applies by spraying, atomizing, dusting, broadcasting or watering. The use form depends on the intended purpose; in any case, it should ensure as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and derivatives thereof with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or jointly grinding the compounds I, II or III or the mixture of the compounds I, II and III with a solid carrier.

Granules (eg. coated granules, impregnated granules or homogeneous granules) are usually prepared by binding the active ingredient, or the active ingredients, to a solid carrier.

Fillers or solid carriers are, for example, mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, and fertilizers such ammonium sulfate, ammonium phosphate, ammonium nitrate and ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I, II, or III or of the mixture of the compounds I, II, and II. The active ingredients are employed in a purity of from 90% to 100%, preferably 95% to 100% (according to NMR spectrum or HPLC).

The compounds I, II or III, or the mixtures, or the corresponding formulations, are applied by treating the harmful fungi, their habitat, or the plants, seeds, soils, areas, materials or spaces to be kept free from them, with a fungicidally effective amount of the mixture, or of the compounds I, II and III in the case of separate application. Application can be effected before or after infection by the fungi.

USE EXAMPLES

The synergistic activity of the mixtures according to the invention was demonstrated by the following experiments:

A) Activity Against Powdery Mildew of Wheat

Leaves of potted wheat seedlings of the variety "Frühgold" were sprayed to runoff point with an aqueous formulation of active ingredient prepared from a stock solution consisting of 10% of active ingredient, 63% of cyclohexanone and 27% of emulsifier. 24 hours after the spray coating had dried on, the leaves were dusted with spores of powdery mildew of wheat (Erysiphe graminis forma specialis tritici). The test plants were subsequently kept in a greenhouse at 20–24° C. and 60–90% relative atmospheric humidity. After 7 days, the extent of the mildew development was determined visually in % infection of the total leaf area.

Evaluation was carried out by determining the affected leaf areas in percent. These percentages were converted into efficacies. The efficacy (E) was calculated as follows using Abbot's formula:

$$E = (1-\alpha) \cdot 100/\beta$$

$\alpha$ corresponds to the fungal infection of the treated plants in % and $\beta$ corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active ingredients were determined using Colby's formula [R. S. Colby, Weeds 15, 20–22 (1967)] and compared with the observed efficacies.

Colby's formula $$E = x+y+z-x\cdot y\cdot z/100$$

E expected efficacy, expressed in % of the untreated control, when using the mixture of the active ingredients A, B and C at the concentrations a, b and c x efficacy, expressed in % of the untreated control, when using active ingredient A at a concentration of a y efficacy, expressed in % of the untreated control, when using active ingredient B at a concentration of b z efficacy, expressed in % of the untreated control, when using active ingredient C at a concentration of c The results are shown in Tables 4 and 5 below.

TABLE 4

| Ex. | Active ingredient or mixture | Concentration of active ingredient in the spray liquor in ppm | Efficacy in % of the untreated control |
|---|---|---|---|
| 1C | Control (untreated) | (97% infection) | 0 |
| 2C | I/1 (Compound Ia.32 from Tab. 1) | 1.25 | 0 |
|  |  | 0.31 | 0 |
| 3C | I/2 (Compound Ia.38 from Tab. 1) | 1.25 | 0 |
|  |  | 0.31 | 0 |
| 4C | Mixture of IIa + III.1-6 | 1.25 IIa + 1.25 III.1-6 | 0 |
| 5C | Mixture of IIa + III.1-6 | 0.31 IIa + 0.31 III.1-6 | 0 |
| 6C | Mixture of IIa + III.1-1 | 0.31 IIa + 0.31 III.1-1 | 69 |
| 7C | Mixture of IIb + III.1-6 | 0.31 IIb + 0.31 III.1-6 | 7 |
| 8C | Mixture of IIb + III.1-1 | 0.31 IIb + 0.31 III.1-1 | 79 |

TABLE 5

| Ex. | Mixture according to the invention | Observed efficacy | Calculated efficacy*) |
|---|---|---|---|
| 9 | 1.25 ppm I/1 + 1.25 ppm IIa + 1.25 ppm III.1-6 | 49 | 0 |
| 10 | 0.31 ppm I/1 + 0.31 ppm IIa + 0.31 ppm III.1-6 | 30 | 0 |
| 11 | 1.25 ppm I/2 + 1.25 ppm IIa + 1.25 ppm III.1-6 | 49 | 0 |
| 12 | 0.31 ppm I/2 + 0.31 ppm IIa + 0.31 ppm III.1-6 | 27 | 0 |
| 13 | 0.31 ppm I/1 + 0.31 ppm IIa + 0.31 ppm III.1-1 | 95 | 69 |
| 14 | 0.31 ppm I/1 + 0.31 ppm IIb + 0.31 ppm III.1-6 | 28 | 7 |
| 15 | 0.31 ppm I/1 + 0.31 ppm IIb + 0.31 ppm III.1-1 | 95 | 79 |

*)calculated using Colby's formula

The test results show that the observed efficacy in all mixing ratios is higher than the efficacy which had been calculated beforehand using Colby's formula.

B) Curative Activity Against Puccinia Recondita on Wheat (Wheat Leaf Rust)

Leaves of potted wheat seedlings of the variety "Frühgold" were dusted with spores of leaf rust (Puccinia recondita). Thereafter, the pots were kept for 24 hours in a chamber of high atmospheric humidity (90 to 95%) and 20 to 22° C. During this time, the spores germinated and the germinal tubes penetrated into the leaf tissue. The next day, the infected plants were sprayed to runoff point with an aqueous formulation of active ingredient prepared from a stock solution consisting of 10% of active ingredient, 63% of cyclohexanone and 27% of emulsifier. After the spray coating had dried on, the test plants were cultivated in a greenhouse at from 20 to 22° C. and from 65 to 70% of relative atmospheric humidity for 7 days. Thereafter, the extent of rust fungus development on the leaves was determined visually.

The visually determined percentages of infected leaf areas were converted into efficacies as % of the untreated control. An efficacy of 0 means the same disease level as in the untreated control, an efficacy of 100 means a disease level of 0%. The expected efficacies for active compound combinations were determined using Colby's formula (Colby, S. R.: "Calculating synergistic and antagonistic responses of herbicide Combinations", Weeds 15, p. 20–22, 1967) as described for Examples 1–15 and compared to the observed efficacies.

The test results are shown in Tables 6 and 7 below.

TABLE 6

| Ex. | Active ingredient or binary mixture | Concentration of active ingredient in the spray liquor in ppm | Efficacy in % of the untreated control |
|---|---|---|---|
| 16C | Control (untreated) | (93% infection) | 0 |
| 17C | Compound I/1 (cf. Ex. 2C) | 1.25 | 47 |
|  |  | 0.31 | 0 |
| 18C | Compound I/2 (cf. Ex. 3C) | 0.31 | 0 |
| 19C | Compound Ib | 0.31 | 0 |
| 20C | Mixture of IIa + III.1-6 | 0.31 IIa + 0.31 III.1-6 | 0 |
| 21C | Mixture of IIa + III.1-1 | 0.31 IIa + 0.31 III.1-1 | 0 |
| 22C | Mixture of IIb + III.1-6 | 0.31 IIb + 0.31 III.1-6 | 4 |
| 23C | Mixture of IIb + III.2-7 | 1.25 IIb + 1.25 III.2-7 | 4 |
| 24C | Mixture of IIb + III.2-7 | 0.31 IIb + 0.31 III.2-7 | 0 |
| 25C | Mixture of IIb + III.1-1 | 0.31 IIb + 0.31 III.1-1 | 0 |

TABLE 7

| Ex. | Mixture according to the invention | Observed efficacy | Calculated efficacy*) |
|---|---|---|---|
| 26 | 0.31 ppm I/1 + 0.31 ppm IIa + 0.31 ppm III.1-6 | 95 | 0 |
| 27 | 0.31 ppm I/2 + 0.31 ppm IIa + 0.31 ppm III.1-6 | 89 | 0 |
| 28 | 0.31 ppm Ib + 0.31 ppm IIa + 0.31 ppm III.1-6 | 95 | 0 |
| 29 | 0.31 ppm I/1 + 0.31 ppm IIa + 0.31 ppm III.1-1 | 35 | 0 |
| 30 | 0.31 ppm I/2 + 0.31 ppm IIa + | 68 | 0 |

TABLE 7-continued

| Ex. | Mixture according to the invention | Observed efficacy | Calculated efficacy*) |
|---|---|---|---|
| 31 | 0.31 ppm Ib +<br>0.31 ppm IIa +<br>0.31 ppm III.1-1 | 35 | 0 |
| 32 | 0.31 ppm I/1 +<br>0.31 ppm IIb +<br>0.31 ppm III.1-6 | 95 | 4 |
| 33 | 0.31 ppm I/2 +<br>0.31 ppm IIb +<br>0.31 ppm III.1-6 | 95 | 4 |
| 34 | 0.31 ppm Ib +<br>0.31 ppm IIb +<br>0.31 ppm III.1-6 | 93 | 4 |
| 35 | 0.31 ppm I/1 +<br>0.31 ppm IIb +<br>0.31 ppm III.2-7 | 93 | 49 |
| 36 | 0.31 ppm I/1 +<br>0.31 ppm IIb +<br>0.31 ppm III.2-7 | 40 | 0 |
| 37 | 0.31 ppm Ib +<br>0.31 ppm IIb +<br>0.31 ppm III.2-7 | 30 | 0 |
| 38 | 0.31 ppm I/1 +<br>0.31 ppm IIa +<br>0.31 ppm III.1-1 | 40 | 0 |
| 39 | 0.31 ppm I/2 +<br>0.31 ppm IIb +<br>0.31 ppm III.1-1 | 35 | 0 |
| 40 | 0.31 ppm Ib +<br>0.31 ppm IIb +<br>0.31 ppm III.1-1 | 40 | 0 |

*)calculated using Colby's formula

The test results show that the observed efficacy in all mixing ratios is higher than the efficacy which had been calculated beforehand using Colby's formula.

What is claimed is:

1. A fungicidal composition comprising synergistically effective amounts of a) a first active component I selected from the group of
a.1) carbamates of formula I.a,

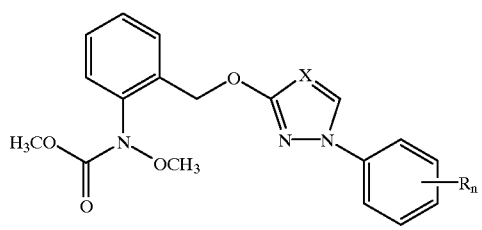

wherein X is CH or N, n is 0, 1 or 2, R is halogen, $C_1$–$C_4$-alkyl or $C_1$–$C_4$-haloalkyl, and the radicals R are identical or different when n is 2, and salts and adducts thereof, and a.2) the oxime ether carboxamide of the formula I.b

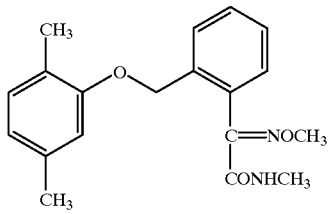

and b) a second active component II selected from the group of b.1) 4-[2-methyl-3-(4-tert-butylphenyl)propyl]-2,6-dimethylmorpholine

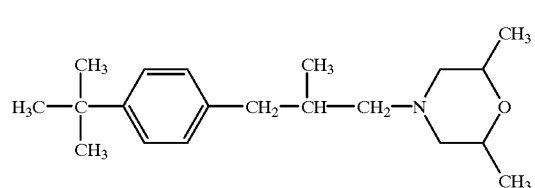

b.2) 4-($C_{10}$–$C_{13}$-alkyl)-2,6-dimethylmorpholine

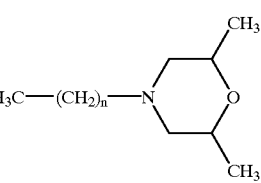

[$n$ = 10, 11, 12(60–70%), 13]

and b.3) (RS)-1-[3-(4-tert-butylphenyl)-2-methylpropyl]-piperidine

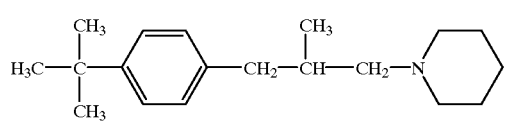

and c) a third active component (III) selected from the group of methyl phenylacetates of formula III.1

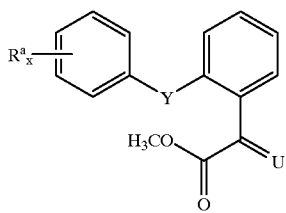

wherein U is CHOCH$_3$ or NOCH$_3$, R$^a$ is cyano, halogen, C$_1$–C$_4$-alkyl or C$_1$–C$_4$-haloalkyl, x is 1, 2 or 3, and the radicals R$^a$ are identical or different when x is 2 or 3, and Y is OCH$_2$ or O-(4,6-pyrimidinyl)-O.

2. The composition defined in claim 1, wherein the component I and the component II are present in a weight ratio of from 10:1 to 0.01:1.

3. The composition defined in claim 1, wherein the component I and the component III are present in a weight ratio of from 10:1 to 0.01:1.

4. The composition defined in claim 1 which is conditioned in two parts, a first part comprising component I in a solid or liquid carrier, and a second part comprising component II in a solid or liquid carrier, and the first or the second part additionally comprising component III.

5. The composition defined in claim 1 which is conditioned in three parts, a first part comprising component I in a solid or liquid carrier, a second part comprising component II in a solid or liquid carrier and a third part comprising component III in a solid or liquid carrier.

6. A method of controlling harmful fungi, which comprises treating the harmful fungi, their habitat, or plants, seeds, soils, areas, materials or spaces to be kept free from said fungi with synergistically effective amounts of components I, II and III as set forth in claim 1.

7. The method of claim 6, wherein components I, II and III are applied simultaneously, that is either together or separately, or in succession.

8. The method of claim 6, wherein component I is applied in an amount of from 0.01 to 2.5 kg/ha.

9. The method of claim 6, wherein component II is applied in an amount of from 0.01 to 10 kg/ha.

10. The method of claim 6, wherein component III is applied in an amount of from 0.01 to 10 kg/ha.

\* \* \* \* \*